United States Patent [19]

Karczewski

[11] 4,133,311

[45] Jan. 9, 1979

[54] ANKLE SUPPORT STRUCTURE

[76] Inventor: Robert A. Karczewski, P.O. Box 651, Middleboro, Mass. 02346

[21] Appl. No.: 794,027

[22] Filed: May 5, 1977

[51] Int. Cl.$^2$ ............................................. A61F 13/06
[52] U.S. Cl. ................................. 128/166; 128/80 H
[58] Field of Search .................... 128/166, 165, 80 H, 128/157, 166.5

[56] References Cited

U.S. PATENT DOCUMENTS

| 3,073,305 | 1/1963 | Biggs, Jr. et al. | 128/166 |
| 3,506,000 | 4/1970 | Baker | 128/166 |
| 3,674,023 | 7/1972 | Mann | 128/166 |
| 3,699,959 | 10/1972 | Garrahan et al. | 128/166 |

Primary Examiner—John D. Yasko
Attorney, Agent, or Firm—Cesari and McKenna

[57] ABSTRACT

A reusable ankle support structure comprises an inner layer of a resilient material, such as neoprene rubber, and an outer layer of a relatively non-resilient but flexible material, such as denim cloth, that is secured as a pair of mirror image sections to the outside surface of the inner layer. Each of the outer layer sections includes an integral, elongated flexible strap extending therefrom. The resilient inner layer is snugly wrapped around the ankle of a human with the straps to the front of the ankle. The straps are snugly wrapped around the foot crossing over the top of the foot and again under the arch of the foot, pulled upwardly on opposite sides of the ankle and then secured under tension to the sides of the structure. The straps thus combine with the inner layer to provide stirrup-like support against eversion and inversion of the ankle. Hook and loop fastening panels may be secured to the structure to facilitate its application.

9 Claims, 2 Drawing Figures

ANKLE SUPPORT STRUCTURE

BACKGROUND OF THE INVENTION

1. Field of the Invention

This invention relates generally to supports for body members and, more particularly, to a reusable support structure for the ankle of a human.

2. Description of the Prior Art

Ankle injuries are common among humans who engage in athletic and other strenuous activities. The human ankle consists of three bones (i.e., the tibia or shin bone, the fibula and the talus) bound together and to the bones of the foot by ligaments. The three bones are independently configured and relatively oriented and spaced to provide freedom of movement of the foot in several degrees relative to the lower leg. The ligaments serve as elastic restrainers to limit that movement.

Injuries result when the strains placed on the ankle exceed the normal limits of movement. These injuries vary widely in severity from simple ligament pulls to ligament ruptures and bone fractures. The most common injuries result from what are known as eversion and inversion of the ankle. Eversion results when the foot rolls over and the ankle moves outwardly relative to the foot. Inversion results when the foot rolls in the opposite direction causing the ankle to move inwardly relative to the foot.

For individuals, particularly athletes who have had a past history of weak or injured ankles, it has been a common practice to tape their ankles with medical adhesive tape to provide added support thereto against eversion and inversion. Taping, though generally recognized as effective in supporting a weak ankle, has several drawbacks. First, medical adhesive tape is expensive and usually not reusable. It can thus be extremely costly to use for individuals who regularly engage in activities requiring ankle support and for organizations that supply such individuals. It is also generally difficult for an individual to apply adhesive tape to his or her own ankle. Taping is thus, on many occasions, not used when it should be used because of the unavailability of a second individual to apply the tape. Also, one who applies tape to another's ankle must generally have a reasonable degree of skill or experience in that regard, for the improper application of the tape can render the taping ineffective and result in other injuries to the ankle and foot, such as irritations of the skin or poor circulation. Moreover, when tape is applied to prevent eversion and inversion of the ankle, it also tends to restrict the forward flexibility of the foot relative to the ankle and thus to limit the ankle's performance.

Because of the above drawbacks, fabric ankle wraps are occasionally used as a substitute for taping. Fabric wraps have the advantage of being reusable and thus tend to be more economical to use. Wraps, however, do not generally provide the support that is provided by properly applied adhesive tape. Typically, the wrap material is such that it tends to slip easily relative to the skin. Slippage causes loosening of the wrap with time and gradually diminishes the amount of support provided by the wrap.

A variety of support structures for the ankle and other parts of the body have been previously proposed as substitutes for medical taping and wraps. These structures vary widely in complexity and cost. None of these structures has found any widespread use or acceptance. Most of the simpler structures provide no real support against eversion and inversion of the ankle. The more complicated structures are generally more effective in this regard but also typically expensive and difficult for an individual to apply to his or her own ankle.

OBJECTS OF THE INVENTION

It is, therefore, a primary object of this invention to provide an improved support structure for a body member such as a human ankle.

Another object of the invention is to provide an ankle support structure that has a relatively simple and inexpensive construction and that is reusable.

Another object of the invention is to provide an ankle support structure of the type described that provides effective support against injury caused by both eversion and inversion of the ankle, but that allows essentially free forward flexibility of the foot relative to the ankle.

Another object of the invention is to provide an ankle support structure of the type described that can be applied by an individual to his or her own ankle with relative ease.

Another object of the invention is to provide an ankle support structure of the type described that, when applied to the ankle, serves to retain body heat in the ankle thus keeping the ankle tissue, muscles, ligaments and the like warm and flexible.

Still another object of the invention is to provide an ankle support structure of the type described that, when applied to the ankle, resists slippage relative to the skin and thus tends to maintain its support for long periods of time.

SUMMARY OF THE INVENTION

Briefly, an ankle support structure fabricated in accordance with the invention comprises an inner, ankle enveloping layer of a relatively resilient material and an outer, relatively non-resilient but flexible layer that is secured to the outside surface of the inner layer. The outer layer includes a pair of elongated flexible straps that project outwardly in essentially opposite directions from the respective lower ends of the inner layer.

The inner layer of the support structure is dimensioned so that it can be snugly wrapped completely around the upper part of the ankle and suitably secured there. The straps are dimensioned and located so that they can be overlapped in a crossing fashion over the top of the foot, wrapped around the foot and again overlapped and crossed under the arch of the foot. The straps are then firmly pulled upwardly along the respective sides of the ankle essentially parallel to the axis of the leg and suitably secured to the sides of the structure. The straps thus provide a stirrup-like support that resists eversion and inversion of the ankle but that allows essentially free forward flexibility of the foot relative to the ankle.

In a preferred embodiment of the invention, panels of hook and loop fastening material are secured at various locations on the support structure that facilitate the application of the structure and make it possible for an individual to apply the structure to his or her own ankle with relatively little effort. The fastening panels are of a sufficient size to permit adjustment of the structure so that each individual can achieve a snug, but comfortable fit. The inner layer is preferably formed from a material, such as neoprene rubber, that resiliently envelopes the ankle and clings to the skin thus avoiding loosening of the structure on the ankle. The neoprene rubber layer also has therapeutic value in that it retains body heat in the ankle which keeps the ankle warm and flexible, thus helping to prevent further injury, and which promotes circulation and healing. The outer layer and straps are preferably formed from cloth fabric, such as denim, which is both strong, durable and washable, and in two separate sections so as not to unduly limit the resiliency of the inner layer.

BRIEF DESCRIPTION OF THE DRAWING

The foregoing and other objects, features and advantages of the invention will be better understood from the following detailed description taken in conjunction with the accompanying drawing in which.

DETAILED DESCRIPTION OF PREFERRED EMBODIMENT

Figure 2:
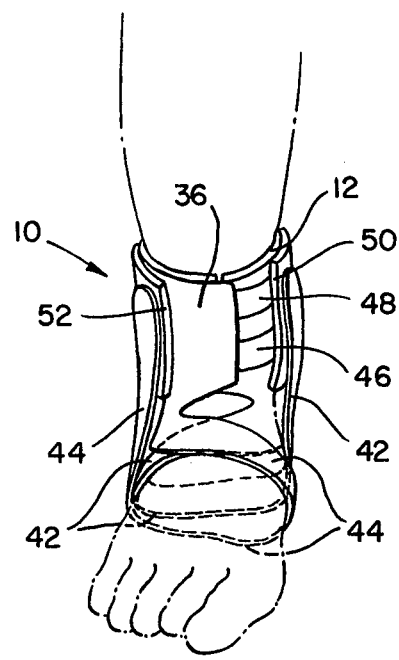
FIG. 2 is a pictorial view showing the support structure of FIG. 1 applied to the ankle of a human.

Referring now specifically to the drawing, there is shown a support structure 10 embodying the invention and adapted for application to the ankle of a human. The structure 10 comprises a bottom or inner layer 12 which is formed of a relatively resilient material, such as neoprene rubber, and which is dimensioned and shaped to resiliently envelope the ankle in the manner shown in FIG. 2 and described more fully below.

Figure 1:
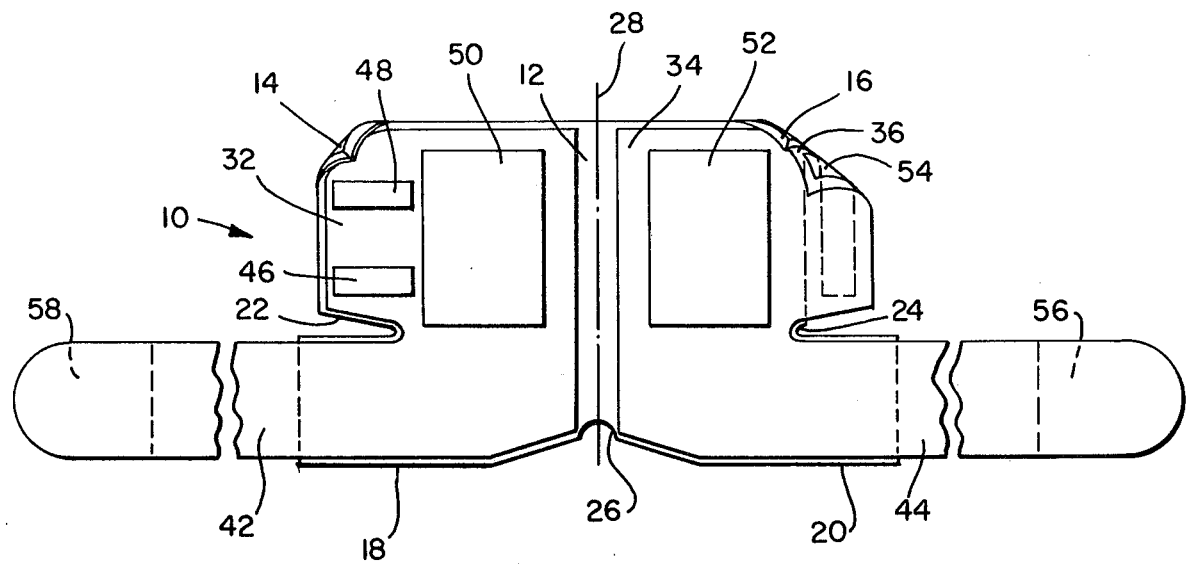
FIG. 1 is a pictorial view of the outside surface of an ankle support structure embodying the invention with various portions thereof folded over so as to reveal its inside surface.

As best seen in FIG. 1, the inner layer 12 of the structure 10 includes left and right side members 14 and 16, respectively, and left and right strap members 18 and 20, respectively, that extend in opposite directions at the lower end of the layer 12. A "V" shaped, inwardly directed cut 22 and 24 is made in each side of the layer 12 between the side and strap members thereof. The cuts 22 and 24 facilitate the outward displacement of the strap members 18 and 20 relative to their corresponding side members 14 and 16 and hence provide a more comfortable, less irritating fit at the junction of the front of the ankle and upper part of the foot.

A rounded, upwardly directed cut 26 is made at the bottom center of the layer 12. The cut 26 is adapted to straddle the Achilles' tendon and upper heel at the rear of the foot and to provide a more comfortable, less irritating fit at that location. The cut 26, by enveloping the Achilles' tendon and heel, also serves to resist slipping and twisting of the layer 12 on the ankle. Additionally, the cut 26 has been found to improve the fit of the wearer's shoe over the structure 10 and to prevent the riding up of the structure 10 inside the shoe.

As indicated in FIG. 1, the layer 12 is preferably formed in a single piece that is essentially symmetrical in shape about a center line 28 except for the fact that the right side member 16 is somewhat smaller in width than the left side member 14. This difference in the width of the side members 14 and 16 helps to avoid the overlap of the side members when the structure 10 is wrapped around the ankle.

A pair of mirror-image outer layer sections 32 and 34 are secured to the outside surface of the inner layer 12. The sections 32 and 34 are preferably formed from a relatively non-resilient, flexible material that is durable, washable and strong. White denim cloth has been found to be admirably suited for the fabrication of the sections 32 and 34.

Both of the sections 32 and 34 are preferably cut to a peripheral shape that matches the peripheral shape of the left hand portion of the inner layer 12. Because the right side member 16 is narrower than the left side member 14 of the layer 12, the right section 34 extends beyond the right side member 16 to provide a flexible flap 36. The two separate outer layer sections 32 and 34 leave the center portion of the inner layer 12 exposed and thus do not unduly limit the resiliency of the inner layer 12.

The sections 32 and 34 may be secured to the inner layer 12 in any suitable manner. A high strength, rubber bond adhesive may, for example, be used for this purpose. The adhesive used is preferably such that it stays relatively flexible and resilient when dry.

Extending outwardly from each of the outer layer sections 32 and 34 is an elongated, flexible strap 42 and 44, respectively. In the preferred embodiment shown in the drawing, the straps 42 and 44 are actually integral extensions of the outer layer sections 32 and 34 that extend beyond the respective ends of the strap members 18 and 20 of the inner layer 12. The straps 42 and 44 are made of sufficient length so that they are capable of wrapping around the foot and then extending upwardly to the upper end of the inner layer 12, in the manner shown in FIG. 2. Typically, each of the straps 42 and 44 extends beyond the end of its associated side member 14 and 16 through a distance equal to about twice the overall height of the inner layer 12.

Panels 46, 48, 50, 52, 54, 56 and 58 of hook and loop fastening material of the type available commercially under the trademark Velcro ® may be secured to various parts of the structure 10 for use in securing the structure 10 to the ankle. For example, the panels 46, 48, 50 and 52, which are secured to the outside of the outer layer sections 32 and 34, may be formed of loop material. The panels 54, 56 and 58, which are secured to the inside surface of the flap 36 and to the inside end surfaces of the straps 42 and 44, respectively, may be formed of hook material. The panel 54 thus cooperates with the panels 46 and 48 in securing the inner layer 12 around the ankle. The panels 56 and 58 cooperate with the panels 50 and 52 in securing the ends of the straps 42 and 44 to the sides of the structure 10. Each of the panels 46, 48, 50, 52, 54, 56 and 58 may be fixed in place by any suitable means, such as by stitching.

The structure 10 is applied to the ankle in the following manner. The center inside surface of the inner layer 12 is brought to bear against the rear of the ankle with the cut 26 in the lower part of the layer 12 straddling the Achilles' tendon and upper heel. The side member 14 and flap 36 are then gripped, wrapped toward the front of the ankle and pulled together to stretch the inner layer 12 so as to achieve a snug, but comfortable grip around the ankle. The panel 54 on the flap 36 is then pressed against the panels 46 and 48 to secure the inner layer 12 in place. A single strip of medical adhesive tape may be wrapped around the inner layer 12 to insure against the relative loosening of the panels 54, 46 and 48 during use.

The strap 42 is firmly wrapped over the top of the foot, under the arch of the foot and up along the outside of the ankle essentially parallel to the axis of the leg. After a snug, but comfortable amount of upward tension is applied to the strap 42, the panel 58 on the inside end surface thereof is pressed against the panel 50 to secure the strap 42 in place.

The strap 44 is wrapped around the foot in the opposite direction across the strap 42 at the top and under the arch of the foot and pulled upwardly along the inside of the ankle. After applying snug upward tension on the strap 44, the panel 56 on the inside end surface thereof is pressed against the panel 52 to secure the strap 44 in place. Another single strip of medical adhesive tape may be wrapped about the layer 12 to assist in holding the straps 42 and 44 in place.

The straps 42 and 44 serve as inside and outside stirrups in resisting eversion and inversion of the ankle. Eversion of the ankle is resisted by the axial tension in the strap 42. Inversion of the ankle is resisted by the axial tension in the strap 44. Additionally, the straps 42 and 44 are essentially in a plane that includes the axis of the leg and the pivot point for forward flexibility of the foot relative to the ankle. As a result, they provide a minimal amount of resistance to this flexibility and a minimum amount of interference with the free use of the ankle.

In summary, it can be seen that the above described ankle support structure 10 possesses several attractive features. For example, the structure 10 has a simple, low-cost construction which, when combined with its reusability and durability, makes it an economically attractive alternative to taping. The structure 10 is simple enough to apply that an individual can readily apply it to his or her own ankle. Although various different sizes of the structure 10 may be necessary to accommodate the broad spectrum of ankle sizes for children, women and adults, each structure 10 provides considerable room for adjustment thus enabling the individual to achieve a fit that best suits him or her. Additionally, and perhaps most importantly, the structure 10 provides effective support against the most common causes of ankle injuries but does not unnecessarily interfere with the free use of the ankle.

There are also a couple of advantages that result from the use of a material such as neoprene rubber for the inner layer 12. The surface texture of this material is such that it tends to cling to the skin around the ankle even as the ankle starts to perspire. Consequently, the inner layer 12 holds fast to the ankle and does not loosen after long periods of application. The material also tends to insulate the ankle and retain body heat therein. This heat not only keeps the ankle muscles, ligaments and the like warm and flexible (this resisting pulls and tears), but also promotes healing and circulation in injured ankles.

It should be understood that the above-described ankle support structure 10 is intended to illustrate rather than limit my invention and that numerous modifications can be made thereto without departing from the scope of my invention as defined by the appended claims. For example, the outer layer sections 32 and 34 and straps 42 and 44 could be formed from a material, such as a rubberized fabric, that itself has resiliency and elasticity. The outer layer may also be in the form of a single continuous layer that extends completely across the outside surface of the inner layer 12, rather than in the form of the two separate sections 32 and 34.

Also, to provide even greater support for the ankle, additional straps may be secured to the structure 10. For example, I have found it desirable in some cases to secure a pair of straps to the center rear portion of the outside surface of the inner layer 12 that extend downwardly at a slight outward angle away from the center line 28. After the inner layer 12 is applied to the ankle in the manner described above, a first of these two straps can be wrapped downwardly under the heel along one side of the ankle, firmly pulled upwardly along the opposite side of the ankle and secured to the side of the structure 10. The second of the two straps is then wrapped under the heel in the opposite direction and secured to the other side of the structure 10. These straps form a heel stirrup that gives added support to the rear or heel part of the ankle, and may be recommended for particularly weak or badly injured ankles.

Additionally, a more economical form of the structure 10 can be provided by eliminating the fastening panels 46–58. Such a modified structure could be easily secured to the ankle using a few strips of medical adhesive tape.

It is thus the object of the appended claims to cover these and other modifications as come within the true spirit and scope of the invention.

What I claim as new and desire to secure by Letters Patent of the United States is:

1. A reusable support structure for application to the ankle and foot of a human comprising:
   A. an inner layer
      i. formed of a relatively resilient material,
      ii. having dimensions that enable said layer to be resiliently wrapped around the ankle above the foot, and
      iii. having an inside surface for facing inwardly against the ankle and an outside surface;
   B. an outer layer
      i. comprising first and second separate, essentially mirror image outer layer sections secured in spaced apart positions to the outside surface of said inner layer,
      ii. each of said outer layer sections being formed of a relatively non-resilient, flexible material; and
   C. first and second elongated straps
      i. formed of a relatively non-resilient, flexible material,
      ii. including respective first ends secured to said first and second outer layer sections, respectively, and respective free ends, and
      iii. having respective lengths extending from said outer layer sections that are essentially equal and that enable said first and second straps to be crossed over the top of the foot, wrapped downwardly along first and second opposite sides, respectively, of the foot, crossed under the foot, wrapped upwardly so as to extend essentially parallel to the axis of the leg along the second and first sides, respectively, of the foot and secured under tension in the leg axis parallel position to to said outer layer sections at opposite sides of the ankle, said first and second straps thereby providing a stirrup-like support against eversion and inversion of the ankle.

2. A support structure as recited in claim 1 in which said inner layer includes first and second opposed side members, in which said first side member extends outwardly from the center of said inner layer through a greater distance than said second side member, in which said first outer layer section is secured over said first side member and said second outer layer section is secured over said second side member, and in which said second outer layer section includes an integral flexible flap that extends beyond the end of said second side member, said flexible flap overlapping over said first outer layer section when said inner layer is wrapped around the ankle.

3. A support structure as recited in claim 2 further including a fastening panel of a first type secured to the inside surface of said flexible flap, a fastening panel of a second, cooperating type secured to said second outer layer section for removably securing said flexible flap to said second outer layer section when said inner layer is wrapped around the ankle.

4. A support structure as recited in claim 1 further including a fastening panel of a first type secured to the free end of each of said first and second straps and a pair of fastening panels of a second, cooperating type secured in spaced apart positions to said first and second outer layer sections, respectively, for removably securing said first and second straps to said outer layer sections at opposite sides of the ankle when said straps are wrapped about the foot and ankle to provide stirrup-like support.

5. A support structure as recited in claim 2 in which said inner layer further includes first and second opposed strap members extending outwardly in essentially opposite directions from lower end of said inner layer below said first and second side members and in which said first and second straps extend outwardly from and essentially parallel to said first and second strap members, respectively.

6. A support structure as recited in claim 1 in which the lower, center end portion of said inner layer defines a rounded, upwardly directed cut that straddles the rear part of the ankle and foot when said inner layer is wrapped around the ankle.

7. A support structure as recited in claim 1 in which said inner layer is formed from neoprene rubber.

8. A support structure as recited in claim 1 in which said straps are formed from a relatively non-resilient fabric material.

9. A support structure as recited in claim 1 in which said first outer layer section and said first strap are formed from a single piece of relatively non-resilient fabric material and in which said second outer layer section and said second strap are formed from a single piece of said same relatively non-resilient fabric material.

* * * * *